United States Patent
Bamba et al.

(10) Patent No.: US 10,252,972 B2
(45) Date of Patent: *Apr. 9, 2019

(54) SYNTHESIS OF LONG-CHAIN UNSATURATED FATTY ACID BY CHEMICAL REACTION OF CARBON CHAIN EXTENSION

(71) Applicant: Bizen Chemical Co., Ltd., Akaiwa-shi, Okayama (JP)

(72) Inventors: Naomichi Bamba, Akaiwa (JP); Yoshihisa Misawa, Akaiwa (JP); Hiroshi Tabata, Akaiwa (JP); Yoshio Shimizu, Akaiwa (JP)

(73) Assignee: Bizen Chemical Co., Ltd., Akaiwa-shi, Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/739,533

(22) PCT Filed: Jun. 27, 2016

(86) PCT No.: PCT/JP2016/003084
§ 371 (c)(1),
(2) Date: Dec. 22, 2017

(87) PCT Pub. No.: WO2017/002353
PCT Pub. Date: Jan. 5, 2017

(65) Prior Publication Data
US 2018/0186720 A1 Jul. 5, 2018

(30) Foreign Application Priority Data
Jun. 30, 2015 (JP) .................................. 2015-131053

(51) Int. Cl.
*C07C 33/02* (2006.01)
*C07C 67/32* (2006.01)
(Continued)

(52) U.S. Cl.
CPC ............ *C07C 67/32* (2013.01); *C07C 29/147* (2013.01); *C07C 67/343* (2013.01); *C07C 303/28* (2013.01)

(58) Field of Classification Search
CPC .............................. C07C 67/32; C07C 67/343
(Continued)

(56) References Cited

FOREIGN PATENT DOCUMENTS

JP 48-32082 10/1973
JP 48032082 B2 * 10/1973
(Continued)

OTHER PUBLICATIONS

Haider et al., "Synthesis of Phosphatidylcholine Having a Very Long Chain Polyunsaturated Fatty Acid," *Chemistry Letters*, 2 pages, 1998.

*Primary Examiner* — Deborah D Carr
(74) *Attorney, Agent, or Firm* — Seed IP Law Group LLP

(57) ABSTRACT

A method of chemically extending a carbon chain of an unsaturated fatty acid for conversion into a different unsaturated fatty acid has been reported. The present invention shortens reaction steps of conventional methods, and completes a carbon chain extending reaction in a shorter time. The present invention provides a method of extending a carbon chain of an unsaturated fatty acid by two carbons, comprising steps of four stages including a short-path conversion reaction of an unsaturated fatty chain obtained from an unsaturated fatty acid into a malonic ester derivative, and heating of the malonic ester derivative to reflux in a lower fatty acid solution. The method of the present invention can complete a carbon chain extending reaction in a shorter time.

15 Claims, 2 Drawing Sheets

(51) Int. Cl.
    *C07C 29/147*     (2006.01)
    *C07C 303/28*     (2006.01)
    *C07C 309/66*     (2006.01)
    *C07C 67/343*     (2006.01)
    *C07C 69/587*     (2006.01)
    *C07C 69/602*     (2006.01)

(58) Field of Classification Search
    USPC ........................................................ 554/165
    See application file for complete search history.

(56) References Cited

FOREIGN PATENT DOCUMENTS

| | | | |
|---|---|---|---|
| JP | 08-245508 A | | 9/1996 |
| JP | 08245508 A | * | 9/1996 |
| WO | 03/082792 A1 | | 10/2003 |
| WO | WO2003082792 A1 | * | 10/2003 |
| WO | 2015/115032 A1 | | 8/2015 |

* cited by examiner

SYNTHESIS OF LONG-CHAIN UNSATURATED FATTY ACID BY CHEMICAL REACTION OF CARBON CHAIN EXTENSION

TECHNICAL FIELD

The present invention relates to a short-path chemical synthesis method of unsaturated fatty acids by a carbon chain extending reaction.

BACKGROUND ART

Docosapentaenoic acid is one of rare unsaturated fatty acids, which is C22:5 n-3, contained in fish oil by a slight amount. Mass production of highly pure docosapentaenoic acids is strongly expected for the promotion of physiological/medical/nutritional research (Non Patent Literature 1).

With regard to this point, the following facts have been reported (Non Patent Literature 2).
(1) Docosapentaenoic acid is generated from icosapentaenoic acid in many tissues, and the opposite occurs at the same time.
(2) Docosapentaenoic acid is effective in lowering triglyceride levels.
(3) Docosapentaenoic acid is metabolized in blood platelets to give hydroxydocosapentaenoic acid. Starting with this fact, facts that docosapentaenoic acid is converted in vivo into resolvin D4, which is one of lipid mediators, and this activates the immune system to exhibit anti-inflammatory action, have been made clear one after another.
(4) Docosapentaenoic acid is effective in maintaining and promoting health.
Non Patent Literature 3 reports the following.
(5) The rabbit platelet agglutination inhibitory action of docosapentaenoic acid is stronger than icosapentaenoic acid or docosahexaenoic acid, and a clot formation suppressing effect can be expected.
(6) Docosapentaenoic acid also has an endothelial cell migration capability that is 10-times greater than icosapentaenoic acid. This is an important effect in wound healing.
Non Patent Literature 4 reports the following.
(7) The action of lowering fatty acid synthase and malate synthase activity of docosapentaenoic acid is stronger than icosapentaenoic acid.
(8) Docosapentaenoic acid possibly regulates a phenomenon of sustained improvement in signaling between two nerve cells by aging-related spatial learning and costimulation.
Non Patent Literature 5 reports the following.
(9) Docosapentaenoic acid exerts an angiogenesis suppressing effect.

As discussed above, docosapentaenoic acid would play an important role in fields of alternative medicines and health food in the future, and the demand thereof would accordingly increase. Thus, development of a highly efficient production method by the present invention is an urgent problem to be solved. In recent years, biological functions of polyunsaturated fatty acids, especially icosapentaenoic acid, docosapentaenoic acid and docosahexaenoic acid from fish oil, are gaining increased attention. The demand thereof has been increasing, including high-purity icosapentaenoic acid as a pharmaceutical. In addition, the demand for polyunsaturated fatty acids as supplements such as docosahexaenoic acid having action of improving cranial nerve functions is also expanding. On the other hand, polyunsaturated fatty acid resources are in a declining trend on a global scale, and thus securement of those acids has been explored worldwide as an important problem to be solved. Currently, they mostly depend on fishery resources which are mainly fishes. However, a research related to a method of production using algae and plants is actively pursed. For instance, Monsanto Company established a method of producing stearidonic acid, which is a precursor of icosapentaenoic acid, using genetically modified soybeans, and this is already approved by the FDA. In addition, methods of using a chemical reaction to extend polyunsaturated fatty acids or a microbially produced desaturase have also been reported. However, it is generally difficult to simultaneously conduct reactions of carbon chain extension on polyunsaturated fatty acids in a large scale, and thus said method is not at a stage where it can be practiced in a practical production level beyond a laboratory scale. A synthesis method of polyunsaturated fatty acids by a chemical reaction of carbon chain extension that does not use an enzyme has been reported. For example, in Non Patent Literature 6, one methylene proton in a p-toluenesulfonylmethyl isocyanate molecule is abstracted with a base and the produced carbanion is reacted with saturated fatty acid methyl ester bromide to synthesize isocyanate having a carbon long chain, and a strong base such as sodium hydride is used to similarly replace the other proton of the methylene chain with an unsaturated chain. Lastly, lithium/ammonia/ethanol and methanol/hydrochloric acid are reacted to perform a reaction of removing toluenesulfonyl and a reaction of removing isonitrile to synthesize a polyunsaturated fatty acid methyl ester of interest. However, these methods are disadvantageous in that the total yield is low, and an expensive reagent or a reagent that has strong reactivity and is difficult to handle, must be used.

Meanwhile, Baba et al. have successfully synthesized tetracosahexaenoic acid methyl ester with 2 more carbon atoms than docosahexaenoic acid methyl ester through: using docosahexaenoic acid ethyl ester as a starting material to produce alcohol by lithium aluminum hydride reduction and converting the alcohol into p-toluenesulfonic ester; then converting the p-toluenesulfonic ester into iodide by a substitution reaction; in the presence of a base, further reacting diethylmalonate therewith to produce malonate ester; and subjecting the ester to alkaline hydrolysis, decarboxylation, and methyl esterification (Non Patent Literature 7 and Non Patent Literature 8).

This reaction process was also applied to a carbon chain extending reaction of linoleic acid or arachidonic acid. However, since multistage reaction steps are included, this is not necessarily considered as a practical method for large-scale production.

The method published by Ito et al. in 2011 synthesizes tetracosahexaenoic acid with 2 more carbons in 4 steps from docosapentaenoic acid ethyl ester (Non Patent Literature 9). However, this method uses an explosive reagent that is very unstable to air called DIBAL-H, and a reaction is performed at a low temperature of −78° C. Thus, it is expected that scaling up of the synthesis process would be difficult.

According to references in the 1970s (Non Patent Literatures 10 and 11), a method of converting fatty alcohol into methanesulfonic ester, and introducing diethyl malonate into this has been reported. By employing this method, synthesis of iodide as an intermediate becomes unnecessary, and it is possible to omit one step from the full process. However, in the reaction example carried out in these references in the 1970s, a heating reaction is performed by using high boiling point solvents such as xylene and butanol in a closed system where pressure is applied. Such a reaction condition is not suitable for carbon chain extension of EPA, DPA and DHA, which are unstable to heat. In the present patent, by using dimethylformamide or dimethyl sulfoxide, which is a polar aprotic solvent that activates carbon anion, instead of xylene and butanol, it is possible to synthesize malonate anion having high reactivity more efficiently, and by using this, it is possible to easily synthesize malonic ester derivatives also from methanesulfonic esters of alcohols obtained from EPA, DPA and DHA. By employing this step, it is possible to synthesize DPA EE from EPA EE in more shortened 4 steps.

CITATION LIST

Non-Patent Literature

[NPL 1]
P. D. Nichols, J. Petrie, and S. Singh, Long-chain omega-3 oils—An update on sustainable sources. Nutrients, 2010, 2, 572-585.
[NPL 2]
W. W. Christie, "Resolvins and protections"-Chemistry and Biology, AOCS Lipid Library, Feb. 27, 2013.
[NPL 3]
T. Kanayasu-Toyoda, I. Morita, and S. Murota, Docosapentaenoic acid (22:5, n-3), an elongation metabolite of eicosapentaenoic acid (20:5, n-3), is a potent stimulator of endothelial cell migration on pretreatment in vitro. Prostaglandins, Leucotrienes & EFA's, 1996, 54, 319-325.
[NPL 4]
G. Kaur, D. Cameron-Smith, M. Garg, A. J. Sinclair, Docosapentaenoic acid (22:5 n-3): A review of its biological effects. Progress in Lipid Research, 2011, 50, 28-34.
[NPL 5]
Morita (Tokyo Medical and Dental University) et al., Japanese Journal of Circulation Research, 2002, 25, 5.
[NPL 6]
D. W. Johnson, A synthesis of unsaturated very long chain fatty acids. Chem. Phys. Lipids, 1990, 56, 65-71
[NPL 7]
N. Baba, Md. K. Alam, Y. Mori, S. S. Haider, M. Tanaka, S. Nakajima and N. Baba, A first synthesis of a phosphatidylcholine bearing docosahexaenoic and tetracosahexaenoic acids. J. Chem. Soc. Perkin Trans. 1, 2001, 221-223
[NPL 8]
S. S. Haider, M. Tanaka, Md K. Alam, S. Nakajima, N. Baba, and S. Shimizu, Synthesis of phosphatidylcholine having a very long chain polyunsaturated fatty acid. Chem. Lett., 1998, 17, 5-176
[NPL 9]
T. Itoh, A. Tomiyasu, and K. Yamamoto, Efficient synthesis of the very-long-chain n-3 fatty acids, tetracosahexaenoic acid (C24:6 n-3) and tricosahexaenoic acid (C23:6 n-3). Lipids, 2011, 46, 45-46
[NPL 10]
Howard Sprecher, The synthesis of 1-14C-arachidonate and 3-14C-docosa-7, 10, 13, 16-tetraenoate, Lipids, 889-894, Vol. 6. 1970
[NPL 11]
F. Spener and H. K. Mangold, Reactions of aliphatic methanesulfonates VII. Chain elongation by two methylene groups, Chem. Phys. Lipids, Vol. 11, 215-218, 1973

SUMMARY OF INVENTION

Technical Problem

Methods of converting an unsaturated fatty acid into a different unsaturated fatty acid by chemically extending a carbon chain of the unsaturated fatty acid have been reported. One of such methods is a process of using a synthesis method of malonic ester. The problem to be solved of the present invention is to decrease reaction steps in conventional methods, where malonic ester derivatives are used as intermediates, and complete a carbon chain extending reaction in a shorter time.

Solution to Problem

The present invention decreases types of reactions required in conventional carbon chain extension, and outstandingly shortened the full reaction process. The present inventors completed a novel method of synthesizing a 2 carbon-extended unsaturated fatty acid ester of interest in one step from malonic ester derivatives in the conventional process (PCT/JP2015/000130). In this method, synthesis of malonic ester derivatives from unsaturated alcohols is performed by going through p-toluenesulfonic ester derivatives and iodide derivatives as intermediates. In contrast, the present invention was completed by discovering that an unsaturated fatty acid ester, where a carbon chain of an unsaturated fatty acid is extended by two carbons, can be obtained without going through iodide derivatives, while using methanesulfonic ester which is more easy to synthesize and is more stable as an intermediate as a substitute of p-toluenesulfonic ester, thereby performing short-path synthesis of malonic ester derivatives.

In one aspect of the present invention, a carbon chain extending reaction of an unsaturated fatty acid is performed by a method comprising the steps of: reducing an unsaturated fatty acid ethyl ester and converting this into a primary unsaturated alcohol; converting the alcohol into methanesulfonic ester; converting this methanesulfonic ester into a malonic ester derivative; and converting this malonic ester derivative into an unsaturated fatty acid ester of interest with an extended carbon chain.

In one aspect of the present invention, a method of extending a carbon chain of an unsaturated fatty acid by 2 carbons is provided by using a step of reacting a malonic ester derivative of an unsaturated fatty chain with a lower fatty acid.

According to the present invention, an unsaturated fatty acid or an ester thereof is synthesized into another unsaturated fatty acid with 2 more carbons. The method of the present invention was able to chemically synthesize a docosapentaenoic acid ethyl ester (n-3) from an icosapentaenoic acid ethyl ester (n-3). The method of the present invention was able to obtain each of the following: icosadienoic acid (C20:2 n-6) from linoleic acid (C18:2 n-6); icosatrienoic acid (C20:3 n-3) from α-linolenic acid (C18:3 n-3); dihomo-γ-linolenic acid (C20:3 n-6) from γ-linolenic acid (C18:3 n-6); docosatrienoic acid (C22:3 n-3) from icosatrienoic acid (C20:3 n-3); docosatrienoic acid (C22:3 n-6) from dihomo-γ-linolenic acid (C20:3 n-6); icosatetraenoic acid (C20:4 n-3) from stearidonic acid (C18:4 n-3); docosatetraenoic acid (C22:4 n-6) from arachidonic acid (C20:4 n-6); docosapentaenoic acid (C22:5 n-3) from icosapentaenoic acid (C20:5 n-3); and tetracosahexaenoic acid (C24:6 n-3) from docosahexaenoic acid (C22:6 n-3).

For example, the present invention provides the following.
(Item 1)
A method of extending a carbon chain of an unsaturated fatty acid by 2 carbons, comprising reacting a malonic ester derivative of an unsaturated fatty chain that is produced by reduction of the unsaturated fatty acid or an unsaturated fatty acid ester thereof, with a lower fatty acid.

(Item 2)

The method of item 1, wherein the unsaturated fatty acid is an unsaturated fatty acid with 16-24 carbons.

(Item 3)

The method of item 1, wherein the unsaturated fatty acid is selected from the group consisting of linoleic acid, linolenic acid, arachidonic acid, stearidonic acid, icosatetraenoic acid, icosapentaenoic acid, docosapentaenoic acid, and docosahexaenoic acid.

(Item 4)

The method of item 1, wherein the malonic ester derivative is a derivative selected from the group consisting of a diethyl malonate derivative, dimethyl malonate derivative, diisopropyl malonate derivative, and dibutyl malonate derivative.

(Item 5)

The method of item 1, wherein the malonic ester derivative of the unsaturated fatty chain is produced by: a formation reaction of an unsaturated alcohol by reduction of the unsaturated fatty acid or an ester thereof; a formation reaction of a sulfonic ester derivative of an unsaturated alcohol by reacting the unsaturated alcohol with a sulfonic acid derivative; and a formation reaction of the malonic ester derivative of the unsaturated fatty chain by reacting the sulfonic ester derivative of the unsaturated alcohol with a malonic ester.

(Item 6)

The method of item 5, wherein the sulfonic acid derivative is a derivative selected from: an ester of an acid in which a sulfonate group is bound to methane, ethane, propane, butane, pentane, or alkyl chains having more carbon numbers, or alkyl chains comprising unsaturated bonds; and an ester of an acid in which a sulfonate group is bound to an aromatic ring selected from the group consisting of benzene and toluene.

(Item 7)

The method of item 5, wherein the sulfonic acid derivative is selected from the group consisting of methanesulfonic acid, p-toluenesulfonic acid, and benzenesulfonic acid.

(Item 8)

The method of item 5, wherein the malonic ester is selected from diethyl malonate, dimethyl malonate, diisopropyl malonate, and dibutyl malonate.

(Item 9)

The method of item 1, wherein the lower fatty acid is a fatty acid with 2-7 carbons.

(Item 10)

The method of item 1, wherein the lower fatty acid is selected from the group consisting of formic acid, acetic acid, propionic acid, butyric acid, isobutyric acid, valeric acid, pivalic acid, hydroangelic acid, and isovaleric acid.

(Item 11)

The method of item 1, which is carried out by heated reflux under a nitrogen atmosphere.

(Item 12)

The method of item 1, wherein the malonic ester derivative of the unsaturated fatty chain is produced via a sulfonic ester derivative of unsaturated alcohol that is obtained by reducing an unsaturated fatty acid or unsaturated fatty acid ester.

Advantageous Effects of Invention

The present invention enables large-scale synthesis of rare unsaturated fatty acids, which are minor components included in fish oil and the like, and enables investigation of unknown biological functions thereof. Further, the present invention is expected to have a potential as a method of synthesizing useful unsaturated fatty acids from abundantly-existing plant oil when depletion of fish oil resources occurs in the future. The present inventors were able to efficiently synthesize docosapentaenoic acid from icosapentaenoic acid.

DESCRIPTION OF EMBODIMENTS

Figure 1:
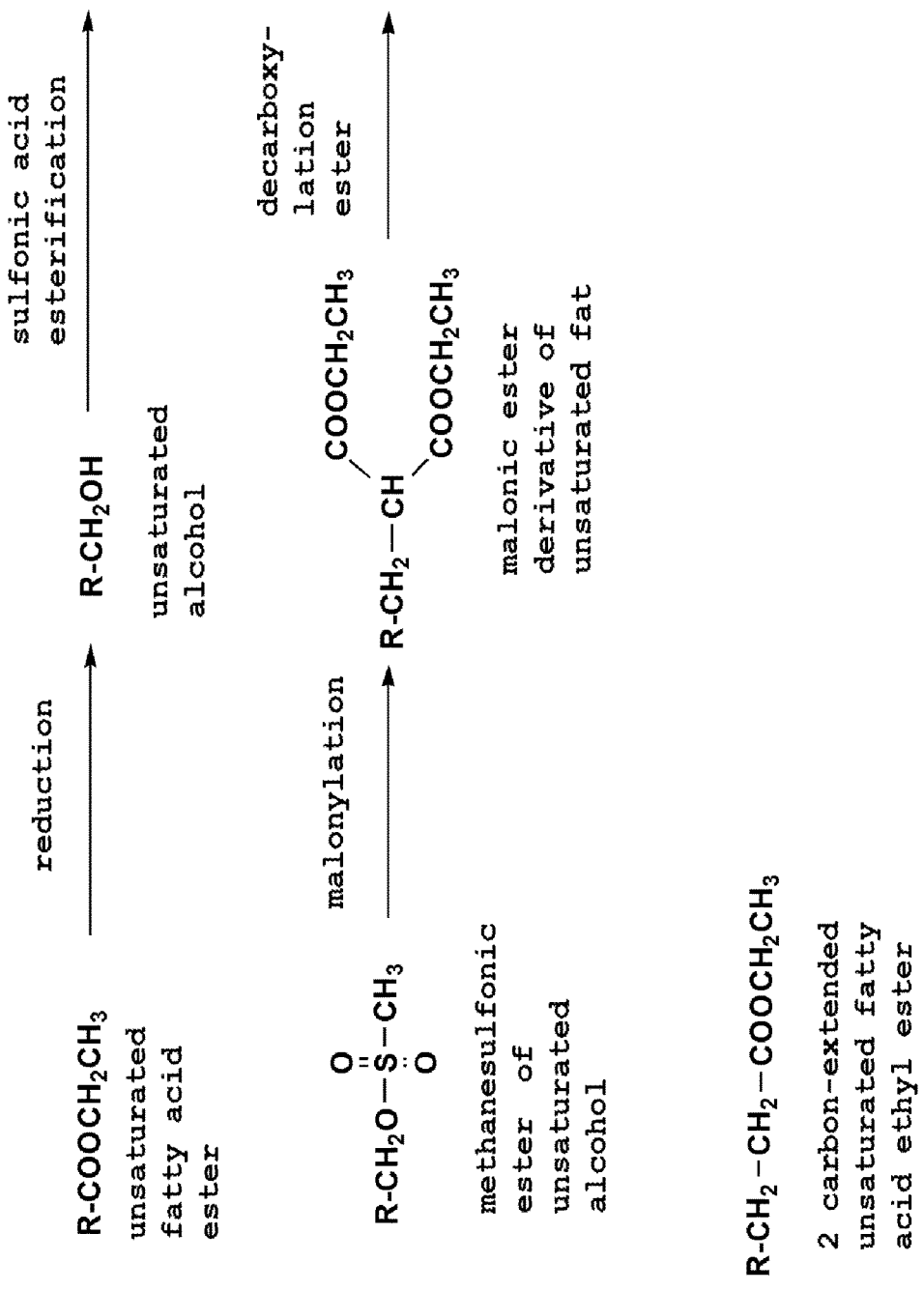
FIG. 1 shows a general diagram of a process of a carbon chain extending reaction of the present invention.
Figure 2:
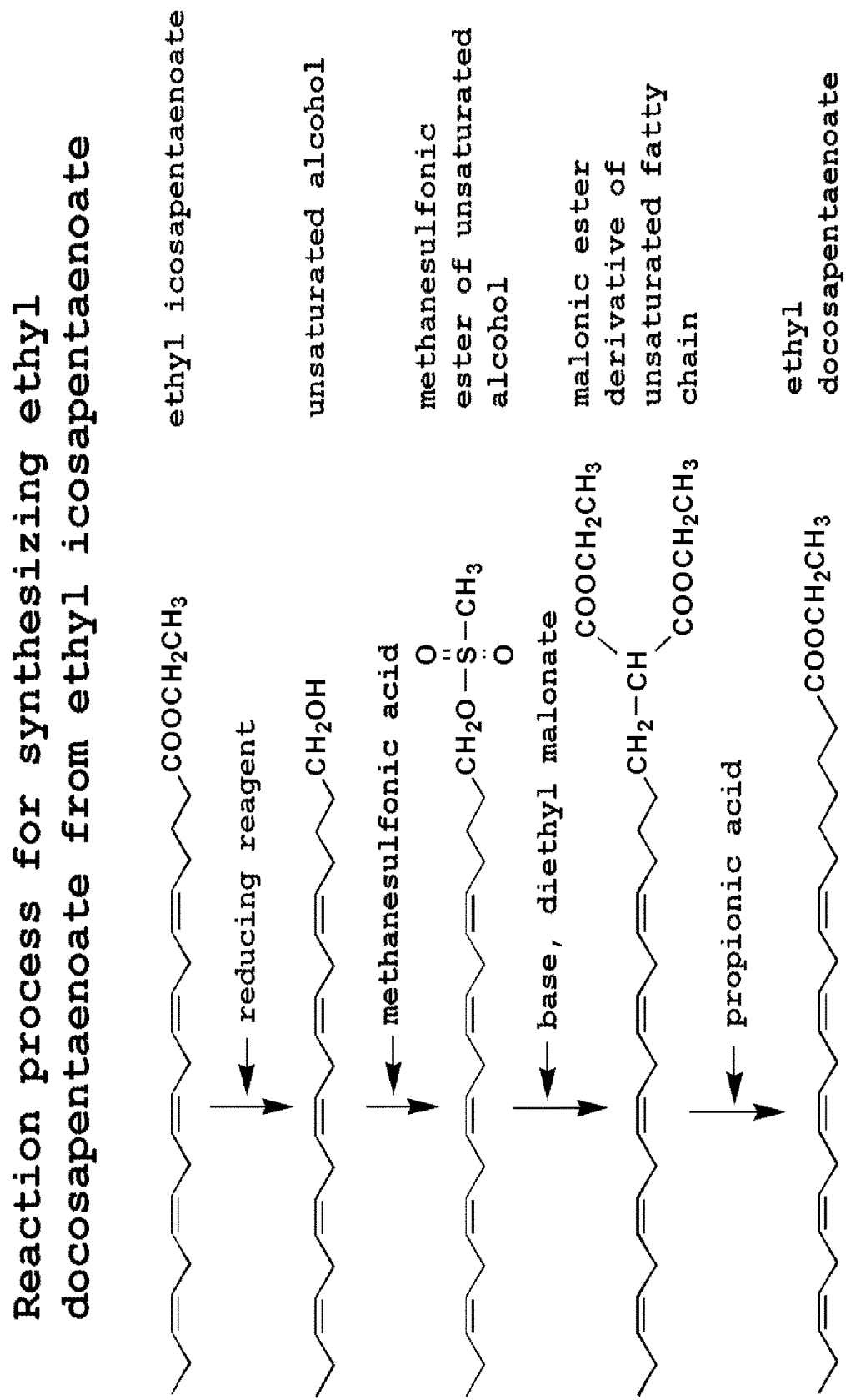
FIG. 2 shows a process of a representative carbon chain extending reaction of the present invention.

Hereinafter, the present invention will be described. Throughout the present specification, it should be understood that unless particularly stated otherwise, an expression in its singular form also includes the conception of plurality. It should be also understood that unless particularly stated otherwise, the terms used in the present specification have the meanings that are conventionally used in the art. Therefore, unless defined otherwise, all technical and scientific terms used in the present specification have the same meanings as commonly understood by those having ordinary skill in the art to which the present invention pertains. In the case of conflict, the present specification, including the definitions, will control. In addition, in the present specification, "wt %" and "percent concentration of mass" can be replaceably used.

Definition of Terms

Hereinafter, the definitions of the terms that are particularly used in the present specification will be listed.

The term "unsaturated fatty acid" as used herein refers to a fatty acid with one or more unsaturated carbon bonds. An unsaturated carbon bond refers to an unsaturated bond between carbons in a molecular chain of carbons, i.e., carbon double bond or triple bond. A naturally-occurring unsaturated fatty acid has one or more double bonds. Substitution thereof with a saturated fatty acid in fat imparts a change in the characteristic of fat such as melting point or fluidity.

In the present invention, an unsaturated fatty acid is preferably a polyunsaturated fatty acid. The number of carbons of the polyunsaturated fatty acid used in the present invention is preferably 16-24, more preferably 17-23, and most preferably 18-22, but is not limited thereto. The polyunsaturated fatty acid used in the present invention comprises preferably 1-7 and more preferably 2-6 double bonds. Examples of polyunsaturated fatty acids include, but are not limited to, linoleic acid, linolenic acid, arachidonic acid, stearidonic acid, icosatetraenoic acid, icosapentaenoic acid, and docosahexaenoic acid.

An unsaturated alcohol is produced by reducing an unsaturated fatty acid or an ester thereof. This unsaturated alcohol reacts with a sulfonic acid derivative to produce a derivative of the unsaturated alcohol such as an ester (sulfonic ester derivative) of the unsaturated alcohol and the sulfonic acid derivative.

Further, in the present invention, a malonic ester derivative of an unsaturated fatty chain is obtained from a reaction between a derivative of an unsaturated alcohol (e.g., a sulfonic ester derivative of an unsaturated alcohol) and a malonic ester. The present invention provides a method of reacting the malonic ester derivative of the unsaturated fatty chain obtained in this manner with a lower fatty acid to extend the carbon chain of the unsaturated fatty acid in the malonic ester derivative by 2 carbons. At the time of this reaction, an antioxidant may or may not be used. This reaction is performed preferably under a nitrogen atmosphere.

Malonic esters that can be utilized in the above-described method of extending a carbon chain of an unsaturated fatty acid by 2 carbons, are ester derivatives of malonic acid, wherein the ester derivatives of malonic acid are substances where alcohol moieties in the molecule do not have dissociable hydrogen. Examples thereof include, but are not limited to, diethyl malonate, dimethyl malonate, diisopropyl malonate, and dibutyl malonate. A "malonic ester derivative of an unsaturated fatty chain", which is a term used herein, is representatively obtained by a reaction between a sulfonic ester derivative of an unsaturated alcohol and a malonic ester of the present invention.

A sulfonic ester derivative of an unsaturated alcohol of the present invention is produced, for example, by a reaction between an unsaturated alcohol and a sulfonic acid derivative. The term "sulfonic acid derivative" as used herein refers to an ester of an acid in which a sulfonate group is bound to methane, ethane, propane, butane, pentane, or alkyl chains having more carbon numbers, or alkyl chains comprising unsaturated bonds; and an ester of an acid in which a sulfonate group is bound to an aromatic ring selected from the group consisting of benzene and toluene, but is not limited thereto. Examples of the sulfonic acid derivative include, but are not limited to, methanesulfonic acid, p-toluenesulfonic acid, and benzenesulfonic acid.

The number of carbons of a lower fatty acid used in the carbon chain extending reaction of the present invention is preferably 2-7, more preferably 2-6, and most preferably 2-5, but is not limited thereto. Examples of the lower fatty acid used in the present invention include, but are not limited to, propionic acid, acetic acid, butyric acid, isobutyric acid, valeric acid, pivalic acid, hydroangelic acid, and isovaleric acid.

The malonic ester derivative used in the method of extending a carbon chain of an unsaturated fatty acid by 2 carbons in a malonic ester derivative of an unsaturated fatty chain of the present invention can be manufactured by any well-known methods.

For example, the present invention can produce a malonic ester derivative of an unsaturated fatty chain by a method comprising:
(a) reducing an unsaturated fatty acid or an ester thereof to produce an unsaturated alcohol;
(b) reacting the unsaturated alcohol with a sulfonic acid derivative (e.g., methanesulfonic acid, p-toluenesulfonic acid, or benzenesulfonic acid) for conversion into an ester (e.g., methanesulfonic ester, p-toluenesulfonic ester, or benzenesulfonic ester) with the sulfonic acid derivative; and
(c) converting the ester with the sulfonic acid derivative into a malonic ester derivative.

For example, subsequently to the above-described steps, the step of
(d) reacting the malonic ester derivative with a lower fatty acid
is further performed in accordance with the present invention to provide a method of extending a carbon chain of an unsaturated fatty acid by 2 carbons.

The above-described step (a) is performed, for example, by reducing a polyunsaturated fatty acid or an ester thereof with lithium aluminum hydride in a dried tetrahydrofuran solvent to produce an unsaturated alcohol. In addition to tetrahydrofuran, a solvent to be used in this reaction can be dimethyl ether, diethyl ether, dipropyl ether, or diisopropyl ether. In addition, instead of lithium aluminum hydride used in this reaction, sodium bis(2-methoxyethoxy)alminium hydride, lithium borohydride, diisobutylalminum hydride, DIBAL, aluminum hydride, sodium borohydride+aluminum chloride, lithium triethylborohydride, Grignard reagents, borane, lithium hydrotriethylborate, sodium triacetoxyborohydride, sodium trimethoxyborohydride, and lithium amidotrihydroborate can be used, but it is not limited thereto. Any solvent can be used as long as it can perform a reduction reaction from an ester to alcohol.

In the above-described step (b), an unsaturated alcohol is reacted with a sulfonic acid derivative (e.g., methanesulfonic acid, p-toluenesulfonic acid, or benzenesulfonic acid) for conversion into an ester (e.g., methanesulfonic ester, p-toluenesulfonic ester, or benzenesulfonic ester) with the sulfonic acid derivative. In addition to the above-described methanesulfonic acid, p-toluenesulfonic acid, and benzenesulfonic acid, an acid in which a sulfonate group is bound to ethane, propane, butane, pentane, or fatty chains having more carbon numbers, or those fatty chains comprising unsaturated bonds and an acid in which a sulfonate group is bound to an aromatic ring such as benzene or toluene can be utilized as the sulfonic acid derivative. By using these acids, a compound having a structural feature of being an ester of these acids is produced.

The above-described step (c) is performed, for example, by reacting a base with diethyl malonate to produce carbanion, and reacting this with the sulfonic acid derivative of the unsaturated alcohol for conversion into a malonic acid derivative (e.g., malonate diester) where an unsaturated fatty chain is bound. In addition, dimethyl malonate, diisopropyl malonate, dibutyl malonate, diisobutyl malonate, di-sec-butyl malonate, and the like can be used instead of diethyl malonate.

In addition, examples of the base include, but are not limited to, sodium hydride, lithium hydride, potassium hydride, lithium hydroxide, sodium hydroxide, potassium hydroxide, sodium amide, lithium amide, and potassium amide.

In the above-described step (d), for example, a malonic ester derivative is used as a solution of a lower fatty acid such as propionic acid, and heated reflux is performed for 1-50 hours under a nitrogen atmosphere to obtain a fatty acid ester of interest which is extended by 2 carbons. In addition, acetic acid, butyric acid, isobutyric acid, valeric acid, pivalic acid, hydroangelic acid, and isovaleric acid can be used instead of propionic acid.

The present invention performs a carbon chain extending reaction based on malonic ester synthesis while replacing each reaction in the synthesis pathway with a more efficient reaction and further incorporating a new reaction, to improve conventional reactions and construct a novel carbon chain extending reaction pathway that has not been recognized before, thereby efficiently synthesizing rare lipids including docosapentaenoic acid or an ethyl ester thereof. For instance, this is a method of manufacturing rare lipids of interest which include docosapentaenoic acid or an ester thereof by: reducing a polyunsaturated fatty acid ethyl ester including icosapentaenoic acid or an ester thereof with lithium aluminum hydride to produce a polyunsaturated alcohol; converting this into a methanesulfonic ester or p-toluenesulfonic ester (or an ester of an acid in which a sulfonic acid group is bound to an alkyl or an alkenyl comprising one or more unsaturated bonds, or an aromatic ring such as benzene or toluene) with a method that does not use pyridine, which is malodorous and difficult to handle; then reacting this with diethyl malonate to synthesize a malonic acid derivative; and heating the propionic acid solution of the derivative (see Reference Document: R. T. Brown and M. F. Jones, Dealoxycarbonylation of representative β-keto-esters and β-diesters in alkanoic acids. J. Chem. Res. (S). 1984, 332-333, FIG. 1).

A conventional method corresponding to the last step in the above includes three stages, i.e., synthesis of dicarboxylic acid by hydrolysis of a malonic acid derivative, synthesis of monocarboxylic acid by decarboxylation under acidic conditions, and ethyl esterification of the carboxylic acid. This method had a problem that oxidative decomposition of unsaturated portions is very likely to occur along the way, and the steps are complicated while the overall yield is also low. The present invention improves shortcomings of the conventional method.

Hereinafter, the present invention will be explained in detail for exemplification. The technical scope of the present invention is set forth by the Claims, and is not limited by the following descriptions.

Synthesis of a malonic ester, which is the main reaction in the synthesis process of the present invention, is a reaction that is widely used in conversion of an organic compound into carboxylic acid with 2 additional carbon atoms, or in the case of fatty chains, synthesis of carboxylic acid extended by 2 carbons or an ester thereof. The present invention is realized by adding improvements to a series of chemical reactions including this reaction.

A synthesis reaction of the present invention is shown in Scheme 1 (FIG. 1). Each of the steps are as follows:
(1) reducing a polyunsaturated fatty acid or an ester thereof with lithium aluminum hydride in a dried tetrahydrofuran solvent to produce an unsaturated alcohol;
(2) in order to convert this alcohol into a malonic ester derivative, converting this alcohol into an ester by a reaction with a sulfonic acid derivative (e.g., methanesulfonic acid);
(3) reacting a base with a malonic acid derivative (e.g., diethyl malonate) to produce carbanion, and reacting this with an ester of the sulfonic acid derivative in the item (2) for conversion into a malonic ester derivative (e.g., malonate diester) where an unsaturated fatty chain is bound; and
(4) as the final step, using the diester as a solution of lower fatty acid such as propionic acid and performing heated reflux for 1-50 hours under a nitrogen atmosphere to obtain an unsaturated fatty acid ester of interest which is extended by 2 carbons. This final step may or may not use an antioxidant.

Polyunsaturated fatty acids or alcohol esters thereof, which are the raw materials in the present invention, are obtained by performing urea treatment, silver nitrate treatment, vacuum distillation, column chromatography including SMB, or a combination thereof on fish, seaweed, microorganisms, plants, or substances obtained by chemical synthesis. Polyunsaturated fatty acids or alcohol esters thereof, which are used as the starting materials of synthesis, are preferably highly pure, but there is no particular problem even if the purity is low, since purification is performed in each stage of synthesis.

The first step is, for example, a conversion reaction from an ester to a primary alcohol using a reducing reagent, lithium aluminum hydride. Among various reducing reagents, lithium aluminum hydride is used at an overwhelmingly high frequency, as a reagent for converting esters to alcohols. This is because the present reagent is highly reactive, while hardly affecting carbon-carbon unsaturated bonds. Due to such properties, the reagent can be used without any problems, for chemical conversion of icosapentaenoic acid, docosahexaenoic acid, and esters thereof into primary alcohols. In addition, any ether without a leaving group such as diethyl ether and tetrahydrofuran can be used as a reaction solvent. After completion of the reaction, a primary alcohol of interest can be readily obtained by: adding excessive ethyl acetate to completely consume lithium aluminum hydride that is left unreacted; degrading alkoxide generated as a byproduct by adding an aqueous solution of caustic soda; filtering the separated hydroxide; and concentrating the filtrate. In addition, a substance of interest with high purity can be readily obtained by performing purification with column chromatography as needed, and this can be used as it is in the next reaction.

The objective of the present invention can be achieved theoretically by replacing a hydroxyl group of an unsaturated alcohol with an ethoxycarbonylmethyl group, $CH_2COOEt$, but in practice, the step discussed below is required. In order to bind another carbon to a carbon atom to which a hydroxyl group is bound, the hydroxyl group must be detached. In order to facilitate detachment of a hydroxyl group, in general, the hydroxyl group is converted into an ester (e.g., methanesulfonic ester), and a malonyl group is further introduced into the ester portion.

A methanesulfonic acid chloride is reacted with a primary alcohol obtained from an unsaturated fatty acid ester, for conversion into a methanesulfonic ester.

Since a malonic ester derivative has a COOEt group derived from malonic acid, this must be removed in order to induce an unsaturated fatty acid extended by 2 carbons.

A general removal method thereof first reacts alkali with a malonic diester derivative for hydrolysis, and heats the produced dicarboxylic acid in acetic acid for decarboxylation. The obtained monocarboxylic acid undergoes a process of being converted into an ethyl ester to obtain the final product of interest. However, in order to avoid such complexity, the present invention has discovered that an unsaturated fatty acid ester of interest which is extended by 2 carbons can be obtained directly from a malonic ester derivative of long chain lipids, by applying the method published by Brown and Jones in 1884. By using this method, the substance of interest is obtained only from heated reflux of a propionic acid solution of the malonic ester derivative of long chain lipids, removal of the solvent, and column purification. In addition, dealkoxycarbonylation is promoted by reaction of propionic acid with a malonic ester derivative and by going through a ketene intermediate.

Hereinafter, the present invention will be explained in more detail with the Examples and the like. However, the present invention is not limited thereto.

EXAMPLES

Example 1

120 ml of dried tetrahydrofuran was put into a 2-liter reaction flask, and 25.8 g (0.68 mol) of lithium aluminum hydride was carefully added thereto. After stirring for 5 minutes with a magnetic stirrer, a dried tetrahydrofuran solution (1000 ml) of 300 g (0.908 mol) of icosapentaenoic acid ethyl ester (98.5% purity) was slowly dripped into this suspension while stirring, such that the reaction would not be too intense. Cooling was performed with ice water as needed. After stirring for one night at room temperature, heated reflux was further performed for 4 hours. The reaction flask was cooled to 0-5° C. from the outside with ice water, and ethyl acetate was slowly dripped in to consume the residual unreacted lithium aluminum hydride until the intense reaction was finished. Subsequently, in order to degrade a reaction complex, a 2N sodium hydroxide aqueous solution was dripped in while stirring, and the dripping was discontinued when a grey insoluble matter began to separate from the reaction solution. This solution was filtered with a filter paper to remove insoluble matters, and the filtrate was washed twice (70 ml×2) with a 2N hydrochloric acid aqueous solution. Subsequently, the filtrate was washed twice with saturated sodium bicarbonate water and twice with saturated saline, and was dried with anhydrous magnesium sulfate. Magnesium sulfate was separated by filtration, and the filtrate was concentrated under reduced pressure. Column purification was performed by using about 800 ml of silica gel (Fuji Silica Gel B40F), with a hexane/ethyl acetate (98:2) mixed solvent as an eluate. The yield was 138.2 g (yield 52.8%).

The above-described alcohol (19.0 g, 0.066 mol) and triethylamine (14.4 g, 0.141 mol) were dissolved in dichloromethane (150 ml), and this was placed in a 1-liter reaction flask equipped with a temperature gauge and a nitrogen gas introduction tube. Then, a dichloromethane (83 ml) solution of a methanesulfonic acid chloride (8.5 g, 0.0742 mol) was gradually added while stirring with a magnetic stirrer at 1-5° C. under a nitrogen atmosphere. Instead of triethylamine, various amines such as trimethylamine, tripropylamine, pyridine, toluidine, and N,N-dimethylaminopyridine can be used. In addition, instead of dichloromethane, organochlorine compounds such as dichloroethane and chloroform can be used. After completing the addition, stirring was performed for one hour at around 1° C. After completion of the reaction, the solution was made acidic with a 1N hydrochloric acid aqueous solution, and was transferred to a separating funnel. The residue obtained by removing the solvent under reduced pressure after separating a dichloromethane layer and performing drying with anhydrous magnesium sulfate, was used in the next reaction as it is.

Sodium hydride (2.34 g) was placed in a reaction flask, and the oil protecting sodium hydride was removed by performing washing for three times with hexane. After adding dried dimethylformamide (47 ml) to this, diethyl malonate (7.39 g, 0.046 mol) was dripped in. Diethylformamide, dimethyl sulfoxide, diethyl sulfoxide, and hexamethylphosphoric triamide can be used instead of dimethylformamide. This solution was heated and stirred for 4 hours at 110° C. under a nitrogen atmosphere. After cooling, the solution was made acidic with a 1N hydrochloric acid aqueous solution, and was transferred to a separating funnel using water (400 ml). The product, malonic ester derivative, was extracted 4 times with hexane and this hexane solution was washed two times with water and dried with anhydrous magnesium sulfate. After removing the solvent, the residue was purified with medium-pressure silica gel column chromatography. The yield was 9.32 g (yield 42.4%).

A propionic acid (230 ml) solution of the above-described malonic ester derivative (21.1 g, 0.0490 mol) was heated to reflux for 48 hours while stirring under a nitrogen atmosphere. The reaction mixture was transferred to a separating funnel while prewashing with hexane (200 ml). Water (500 ml) was added thereto for shaking, and the separated aqueous layer was extracted again with hexane (150 ml). All hexane layers were washed 4 times with water and once with saturated sodium bicarbonate water, and then dried with anhydrous magnesium sulfate. After filtration and concentration, the residue was purified with medium-pressure silica gel column chromatography. The yield was 9.79 g (yield 55.8%).

According to the present invention, rare polyunsaturated fatty acids, which are included in fish oil and the like at an extremely low content, can be chemically synthesized by a carbon chain extending reaction without depending on living organisms or enzymes. If rare polyunsaturated fatty acids can be sufficiently obtained in such a manner, it is expected that they would not only become valuable materials for researching physicochemical properties/biochemical properties and biological functions thereof, but they would also be successful in development as medicaments.

The present invention has been described by referring to particularly preferred embodiments and examples. However, it will be appreciated by those skilled in the art that various modifications can be made on the present invention without departing from the spirit and scope of the present invention.

The invention claimed is:

1. A method of extending a carbon chain of an unsaturated fatty acid by 2 carbons, comprising reacting a malonic ester derivative of an unsaturated fatty chain that is produced by reduction of the unsaturated fatty acid or an unsaturated fatty acid ester thereof, with a lower fatty acid under acidic conditions, wherein the unsaturated fatty acid is an unsaturated fatty acid with 16-24 carbons and comprises 2-6 double bonds, and the lower fatty acid is a fatty acid with 2-7 carbons, wherein the unsaturated fatty acid is selected from the group consisting of linoleic acid, linolenic acid, arachidonic acid, stearidonic acid, icosatetraenoic acid, icosapentaenoic acid, docosapentaenoic acid, and docosahexaenoic acid.

2. The method of claim 1, wherein the malonic ester derivative is a derivative selected from the group consisting of a diethyl malonate derivative, dimethyl malonate derivative, diisopropyl malonate derivative, and dibutyl malonate derivative.

3. The method of claim 1, wherein the malonic ester derivative of the unsaturated fatty chain is produced by: a formation reaction of an unsaturated alcohol by reduction of the unsaturated fatty acid or an ester thereof; a formation reaction of a sulfonic ester derivative of an unsaturated alcohol by reacting the unsaturated alcohol with a sulfonic acid derivative; and a formation reaction of the malonic ester derivative of the unsaturated fatty chain by reacting the sulfonic ester derivative of the unsaturated alcohol with a malonic ester.

4. The method of claim 3, wherein the sulfonic acid derivative is a derivative selected from: an ester of an acid in which a sulfonate group is bound to methane, ethane, propane, butane, pentane, or alkyl chains having more carbon numbers, or alkyl chains comprising unsaturated bonds; and an ester of an acid in which a sulfonate group is bound to an aromatic ring selected from the group consisting of benzene and toluene.

5. The method of claim 3, wherein the sulfonic acid derivative is selected from the group consisting of methanesulfonic acid, p-toluenesulfonic acid, and benzenesulfonic acid.

6. The method of claim 3, wherein the malonic ester is selected from diethyl malonate, dimethyl malonate, diisopropyl malonate, and dibutyl malonate.

7. The method of claim 1, wherein the lower fatty acid is selected from the group consisting of formic acid, acetic acid, propionic acid, butyric acid, isobutyric acid, valeric acid, pivalic acid, hydroangelic acid, and isovaleric acid.

8. The method of claim 1, which is carried out by heated reflux under a nitrogen atmosphere.

9. The method of claim 1, wherein the malonic ester derivative of the unsaturated fatty chain is produced via a sulfonic ester derivative of unsaturated alcohol that is obtained by reducing an unsaturated fatty acid or unsaturated fatty acid ester.

10. A method of extending a carbon chain of an unsaturated fatty acid by 2 carbons, comprising:

reacting a malonic ester derivative of an unsaturated fatty chain with a lower fatty acid under acidic conditions, wherein the unsaturated fatty acid is an unsaturated fatty acid with 16-24 carbons and comprises 2-6 double bonds and the lower fatty acid is a fatty acid with 2-7 carbons, wherein the unsaturated fatty acid is selected from the group consisting of linoleic acid, linolenic acid, arachidonic acid, stearidonic acid, icosatetraenoic acid, icosapentaenoic acid, docosapentaenoic acid, and docosahexaenoic acid, wherein the malonic ester derivative of the unsaturated fatty chain is produced by:

a formation reaction of an unsaturated alcohol by reduction of the unsaturated fatty acid or an ester thereof;

a formation reaction of a sulfonic ester derivative of an unsaturated alcohol by reacting the unsaturated alcohol with a sulfonic acid derivative; and a formation reaction of the malonic ester derivative of the unsaturated fatty chain by reacting, in a polar aprotic solvent, the sulfonic ester derivative of the unsaturated alcohol with a malonic ester.

11. The method of claim 10, wherein the polar aprotic solvent is dimethylformamide.

12. The method of claim 10, wherein the polar aprotic solvent is dimethyl sulfoxide.

13. The method of claim 10, wherein the sulfonic acid derivative is a derivative selected from: an ester of an acid in which a sulfonate group is bound to methane, ethane, propane, butane, pentane, or alkyl chains having more carbon numbers, or alkyl chains comprising unsaturated bonds; and an ester of an acid in which a sulfonate group is bound to an aromatic ring selected from the group consisting of benzene and toluene.

14. The method of claim 10, wherein the sulfonic acid derivative is selected from the group consisting of methanesulfonic acid, p-toluenesulfonic acid, and benzenesulfonic acid.

15. The method of claim 10, wherein the malonic ester is selected from diethyl malonate, dimethyl malonate, diisopropyl malonate, and dibutyl malonate.

* * * * *